United States Patent [19]
Lauk

[11] Patent Number: 5,223,000
[45] Date of Patent: Jun. 29, 1993

[54] MIXTURES OF TRIPHENEDIOXAZINE OLIGOMERS, THEIR PREPARATION AND THE USE THEREOF FOR DYEING COTTON OR COTTON-POLYESTER BLENDS

[75] Inventor: Urs Lauk, Zürich, Switzerland

[73] Assignee: Ciba-Geigy Corporation, Ardsley, N.Y.

[21] Appl. No.: 784,200

[22] Filed: Oct. 28, 1991

[30] Foreign Application Priority Data

Oct. 30, 1990 [CH] Switzerland ............... 3442/90

[51] Int. Cl.$^5$ ............... C07D 498/04; C09B 19/02; C09B 62/02; D06P 1/38
[52] U.S. Cl. ................................ 8/638; 8/531; 8/532; 8/534; 8/917; 8/918; 8/922; 8/924; 544/75; 544/76
[58] Field of Search ........................ 8/532, 638

[56] References Cited

U.S. PATENT DOCUMENTS

| | | | |
|---|---|---|---|
| 4,049,376 | 9/1977 | Le Pape | 8/647 |
| 4,542,213 | 9/1985 | McClelland et al. | 8/658 |
| 4,578,461 | 3/1986 | Jäger | 544/76 |
| 4,874,857 | 10/1989 | Harms | 544/75 |
| 4,990,615 | 2/1991 | Hewk et al. | 544/76 |
| 5,019,134 | 5/1991 | Ridyard et al. | 8/549 |
| 5,059,681 | 10/1991 | Taylor | 534/634 |
| 5,085,668 | 2/1992 | Pelster et al. | 8/549 |
| 5,122,605 | 6/1992 | Pedrazzi | 8/527 |

FOREIGN PATENT DOCUMENTS

| | | |
|---|---|---|
| 0124971 | 11/1984 | European Pat. Off. . |
| 0256650 | 2/1988 | European Pat. Off. . |
| 0356014 | 2/1990 | European Pat. Off. . |
| 3410236 | 10/1985 | Fed. Rep. of Germany . |
| 2228738 | 9/1990 | United Kingdom . |

*Primary Examiner*—A. Lionel Clingman
*Attorney, Agent, or Firm*—Edward McC. Roberts

[57] ABSTRACT

Mixtures of different oligomer compounds of formula (1) are suitable for use as direct dyes for dyeing and printing a wide range of materials, especially cellulose fibers, to give dyeings and prints of good all-round fastness properties:

$$R\underset{R_1}{\diagdown}N-A-X\underset{(SO_2Z)_p}{\overset{(Y)_n}{\diagup}}\overset{R_2}{\underset{O}{\diagup}}\overset{N}{\underset{R_3}{\diagup}}\overset{O}{\underset{N}{\diagup}}\underset{(ZO_2S)_p}{\overset{(Y)_n}{\diagup}}X-A- = \quad (1)$$

$$-N\underset{R_1}{|}B-N\underset{R_1}{|}A-X\underset{(SO_2Z)_p}{\overset{(Y)_n}{\diagup}}\overset{R_2}{\underset{N}{\diagup}}\overset{O}{\underset{R_3}{\diagup}}\overset{N}{\underset{O}{\diagup}}\underset{(ZO_2S)_p}{\overset{(Y)_n}{\diagup}}X-A-N\underset{R_1}{|}R,\Big]_m$$

wherein $R_1$ is hydrogen or unsubstituted or substituted alkyl, cycloalkyl, aryl or aralkyl, R independently has the meaning of $R_1$ or is an unsubstituted or substituted heteroaryl radical or a radical of formula $$R_4-\overset{O}{\underset{\|}{C}}-,$$

wherein $R_4$ is unsubstituted or substituted alkyl, cycloalkyl, aryl, aralkyl or heteroaryl, A is an unsubstituted or substituted alkylene, cycloalkylene, arylene or aralkylene radical, X is $-O-$, $-S-$ or $-N(R_5)-$, wherein $R_5$ is hydrogen or unsubstituted or substituted alkyl, cycloalkyl, aryl or aralkyl, or wherein the group $$R_1-\overset{|}{N}-A-X-$$

is an unsubstituted or substituted heterocyclic radical, Y is $C_1$-$C_4$alkyl, $C_1$-$C_4$alkoxy, halogen, sulfo, carboxy, carbamoyl, N-mono- or N,N-di-$C_1$-$C_4$alkylcarbamoyl, N-phenyl- or N,N-diphenylcarbamoyl, sulfamoyl, N-mono- or N,N-di-$C_1$-$C_4$alkylsulfamoyl or N-phenyl- or N,N-diphenylsulfamoyl, Z is hydroxy or unsubstituted or substituted alkyl, aryl or aralkyl, $R_2$ and $R_3$ are each independently of the other hydrogen, halogen, cyano, $C_1$–$C_4$alkyl, $C_1$–$C_4$alkoxy, unsubstituted or substituted phenyl, benzyl, benzoylamino or phenoxy, sulfo, carboxy, carbamoyl, phenylcarbamoyl or $C_2$–$C_5$alkanoylamino, B is a bivalent organic linking group, m is an integer from 1 to 6 and n and p are each independently of the other 0 or 1, with the proviso that the different compounds of formula (1) of the mixture of oligomers differ solely in the value of m.

29 Claims, No Drawings

MIXTURES OF TRIPHENEDIOXAZINE OLIGOMERS, THEIR PREPARATION AND THE USE THEREOF FOR DYEING COTTON OR COTTON-POLYESTER BLENDS

The present invention relates to novel mixtures of triphenedioxazine oligomers, to their preparation and to the use thereof for dyeing and printing fibre materials, especially textile fibre materials.

Specifically, the invention relates to mixtures of oligomers comprising at least two compounds of formula

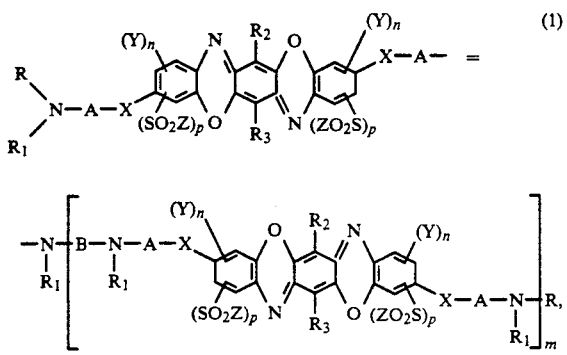

wherein $R_1$ is hydrogen or unsubstituted or substituted alkyl, cycloalkyl, aryl or aralkyl, R independently has the meaning of $R_1$ or is an unsubstituted or substituted heteroaryl radical or a radical of formula

wherein $R_4$ is unsubstituted or substituted alkyl, cycloalkyl, aryl, aralkyl or heteroaryl, A is an unsubstituted or substituted alkylene, cycloalkylene, arylene or aralkylene radical, X is —O—, —S— or —N($R_5$)—, wherein $R_5$ is hydrogen or unsubstituted or substituted alkyl, cycloalkyl, aryl or aralkyl, or wherein the group

is an unsubstituted or substituted heterocyclic radical, Y is $C_1$-$C_4$alkyl, $C_1$-$C_4$alkoxy, halogen, sulfo, carboxy, carbamoyl, N-mono- or N,N-di-$C_1$-$C_4$alkylcarbamoyl, N-phenyl- or N,N-diphenylcarbamoyl, sulfamoyl, N-mono-or N,N-di-$C_1$-$C_4$alkylsulfamoyl or N-phenyl- or N,N-diphenylsulfamoyl, Z is hydroxy or unsubstituted or substituted alkyl, aryl or aralkyl, $R_2$ and $R_3$ are each independently of the other hydrogen, halogen, cyano, $C_1$-$C_4$alkyl, $C_1$-$C_4$alkoxy, unsubstituted or substituted phenyl, benzyl, benzoylamino or phenoxy, sulfo, carboxy, carbamoyl, phenylcarbamoyl or $C_2$-$C_5$alkanoylamino, B is a bivalent organic linking group, m is an integer from 1 to 6 and n and p are each independently of the other 0 or 1, with the proviso that the different compounds of formula (1) of the mixture of oligomers differ solely in the value of m.

$R_1$ as unsubstituted or substituted alkyl radical may be an unsubstituted or substituted $C_1$-$C_6$alkyl radical. Typical examples are a methyl, ethyl, n- or isopropyl or n-, iso-, sec-or tert-butyl radical or a straight-chain or branched pentyl or hexyl radical, which may be substituted by $C_1$-$C_4$alkoxy, which will be understood as meaning throughout this specification typically methoxy, ethoxy, n- or isopropoxy or n-, iso-, sec- or tert-butoxy; hydroxy; sulfo; sulfato; carboxy; cyano; halogen, which will be understood as meaning throughout this specification typically fluoro, bromo and, preferably, chloro; $C_2$-$C_5$alkoxycarbonyl, such as methoxycarbonyl or ethoxycarbonyl; $C_2$-$C_5$alkanoyloxy, such as acetoxy, propionyloxy; or carbamoyl, and/or, with the exception of methyl, which alkyl radical may be interrupted by an —O—, —S— or —NH— group.

Typical examples of suitable alkyl radicals $R_1$ are thus methyl, ethyl, n-propyl, isopropyl, n-, iso-, sec- or tert-butyl, β-chloroethyl, β-hydroxyethyl, β-hydroxybutyl, β-cyanoethyl, sulfomethyl, β-sulfoethyl, β-sulfatoethyl, β-acetoxyethyl, β-sulfatopropyl, γ-sulfatopropyl or the radical of formula —CH$_2$CH$_2$OCH$_2$CH$_2$OH, —CH$_2$CH$_2$NHCH$_2$CH$_2$OH or —CH$_2$CH$_2$OCH$_2$CH$_2$OSO$_3$H.

An alkyl radical $R_1$ is preferably $C_1$-$C_4$alkyl which is unsubstituted or substituted by hydroxy, sulfo, sulfato, chloro, cyano or acetoxy, and/or with the exception of methyl, may be interrupted by a group —O—.

The particularly preferred meaning of $R_1$ as alkyl is an unsubstituted $C_1$-$C_4$alkyl radical and, most particularly, methyl and ethyl.

An unsubstituted or substituted cycloalkyl radical $R_1$ may be unsubstituted or substituted $C_5$-$C_9$-cycloalkyl and, preferably, cyclopentyl or cyclohexyl which is unsubstituted or substituted by $C_1$-$C_4$alkyl, typically in the context of this invention by methyl, ethyl, n- or isopropyl or n-, iso-, sec- or tert-butyl, or by amino, $C_2$-$C_5$alkanoylamino, such as acetylamino or n-propionylamino, or benzoylamino.

The particularly preferred meaning of $R_1$ as cycloalkyl is cyclopentyl or cyclohexyl which is unsubstituted or substituted by 1 to 3 methyl groups, and is most preferably cyclohexyl.

$R_1$ as aryl may be unsubstituted phenyl or naphthyl or phenyl or naphthyl which may be substituted by sulfo, nitro, halogen, cyano, $C_1$-$C_4$alkyl, $C_1$-$C_4$alkoxy, hydroxy, phenoxy, amino, N-mono- or N,N-di-$C_1$-$C_4$alkylamino, $C_2$-$C_5$alkanoylamino, benzoylamino, $C_1$-$C_4$alkoxycarbonyl, carbamoyl, sulfamoyl and/or $C_1$-$C_4$alkylsulfonyl.

$R_1$ as aryl is preferably unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl, or is unsubstituted 1- or 2-naphthyl or 1- or 2-naphthyl which is substituted by sulfo, nitro and/or chloro.

The particularly preferred meaning of $R_1$ as aryl is an unsubstituted phenyl radical or a phenyl radical which is substituted by sulfo, chloro, methyl and/or methoxy.

An aralkyl radical $R_1$ may be unsubstituted or substituted $C_1$-$C_{12}$aralkyl and, preferably, benzylethyl or phenylethyl which may be further substituted by $C_1$-$C_4$-alkyl, sulfo, nitro, halogen or $C_1$-$C_4$-alkoxy. The particularly preferred meaning of $R_1$ as aralkyl is unsubstituted benzyl, or benzyl which is substituted by methyl, sulfo, chloro and/or methoxy, and is most preferably benzyl.

$R_1$ is preferably hydrogen, unsubstituted $C_1$-$C_4$alkyl or $C_1$-$C_4$alkyl which is substituted by hydroxy, sulfo, sulfato, chloro, cyano, or acetoxy and/or, with the exception of methyl, may be interrupted by a group —O—; cyclopentyl or cyclohexyl which are unsubstituted or substituted by 1 to 3 methyl groups; unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl; unsubstituted 1- or 2-naphthyl or 1- or 2-naphthyl which is substituted by sulfo, nitro and/or chloro; or unsubstituted benzyl or benzyl which is substituted by methyl, methoxy, sulfo and/or chloro.

More particularly, $R_1$ is hydrogen, $C_1$-$C_4$alkyl, cyclohexyl, unsubstituted phenyl or benzyl or phenyl or benzyl which are substituted by sulfo, chloro, methyl and/or methoxy, and is most preferably halogen, methyl or ethyl. In a particularly preferred embodiment of the invention $R_1$ is hydrogen.

If R has independently one of the meanings cited above for $R_1$, said meaning comprises the preferred meanings given for $R_1$.

A heteroaryl radical R may be a pyridine, pyrimidine, quinoxaline or triazine radical which carries substituents which are not fibre-reactive.

Suitable substituents on the heteroaryl radical which are not fibre-reactive are typically hydroxy, $C_1$-$C_4$alkyl, phenyl, $C_1$-$C_4$alkoxy, $C_1$-$C_4$alkylthio, amino, or N-mono- or N,N-di-$C_1$-$C_4$alkylamino which are unsubstituted or substituted in the alkyl moiety or moieties by hydroxy, carboxy, cyano, sulfo, sulfato or $C_1$-$C_4$alkoxy; cyclohexylamino; phenylamino or N-$C_1$-$C_4$alkyl-N-phenylamino which are unsubstituted or substituted in the phenyl moiety by $C_1$-$C_4$alkyl, $C_1$-$C_4$alkoxy, phenoxy, carboxy, sulfo and/or halogen; morpholino or 3-carboxy- or 3-carbamoylpyridin-1-yl.

A heteroaryl radical R is preferably a triazinyl radical of formula

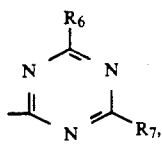

(2)

wherein $R_6$ and $R_7$ are each independently of the other one of the aforementioned substituents which are not fibre-reactive and and which may be the same or different.

$R_4$ as unsubstituted or substituted alkyl, cycloalkyl, aryl or aralkyl has the meanings and preferred meanings given for $R_1$.

A heteroaryl radical $R_4$ may be a quinoxaline or pyrimidine radical.

R is preferably hydrogen, $C_1$-$C_4$alkyl, unsubstituted phenyl or benzyl, or phenyl or benzyl which are substituted by methyl, methoxy, chloro and/or sulfo, or is a radical of formula

wherein $R_4$ is methyl, ethyl or unsubstituted phenyl or phenyl which is substituted by sulfo, chloro, methyl and/or methoxy. Especially preferred meanings of R are methyl, ethyl, benzyl, acetylamino, benzoylamino and, most preferably, hydrogen.

An unsubstituted or substituted alkylene radical A may be an unsubstituted or substituted $C_2$-$C_6$alkylene radical and, preferably, a $C_2$-$C_6$alkylene radical which is unsubstituted or substituted by hydroxy, sulfo, sulfato, $C_1$-$C_4$alkoxy, carboxy, cyano, halogen, phenyl, sulfophenyl or $C_2$-$C_5$alkoxycarbonyl, and/or which may be interrupted by 1 or 2 —O— or —N($R_8$)— groups, wherein $R_8$ is $C_1$-$C_4$alkyl, acetyl or, preferably, hydrogen, or by —S—, —SO$_2$— or a cycloaliphatic or heterocyclic-aliphatic radical.

Exemplary of suitable radicals A are 1,2-ethylene, 1,2- and 1,3-propylene, 1-ethyl-1,2-ethylene, 2-hydroxy-1,3-propylene, 2-sulfato-1,3-propylene, 1- and 2-phenyl-1,3-propylene, 2-(4'-sulfophenyl)-1,3-propylene, 1,4-, 2,3-, and 2,4-butylene, 1,2-dimethyl-1,2-ethylene, 1-phenyl-1,2-ethylene, 2-methyl-1,3-propylene, 2,2-dimethyl-1,3-propylene, 1-chloro-2,3-propylene, 1,5- and 2,4-pentylene, 2-methyl-2,4-pentylene, 1-carboxy-1,5-pentylene, 2,3-diphenyl-1,4-butylene, 1-methoxycarbonyl-1,5-pentylene, 1,6 and 2,5-hexylene, 2-carboxy-1,3-propylene, 2-methoxy-1,3-propylene, a radical of formula —CH$_2$—CH$_2$—Z'—CH$_2$—CH$_2$—, wherein Z' is —O—, —S—, —SO$_2$—, —NH— or —N(CH$_3$)— or a radical of formula

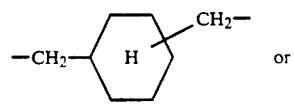

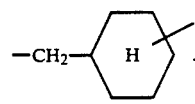

A as alkylene is more particularly a $C_2$-$C_4$alkylene radical which is unsubstituted or substituted by hydroxy, sulfo, sulfato, methoxy, carboxy or sulfophenyl, or —CH$_2$—CH$_2$—Z'—CH$_2$—CH$_2$—, wherein Z' is —O—, —S—, —SO$_2$—, —NH— or —N(CH$_3$)—, especially a $C_2$-$C_4$alkylene radical which is unsubstituted or substituted by hydroxy, sulfo, sulfato, methoxy, carboxy or sulfophenyl and, most preferably, a 1,2-ethylene or 1,2- or 1,3-propylene radical which is unsubstituted or substituted by hydroxy or sulfato. In a particularly preferred embodiment of the invention, A is 1,2-ethylene, 1,2- or 1,3-propylene or 2-sulfato-1,3-propylene.

A as unsubstituted or substituted cycloalkylene may be unsubstituted or substituted $C_5$-$C_9$cycloalkylene and preferably cyclopentylene or cyclohexylene which are unsubstituted or substituted by one or more $C_1$-$C_3$alkyl groups. Most preferably A is unsubstituted cyclohexane or cyclohexylene which is substituted by 1 to 3 methyl groups.

Typical examples of suitable cycloaliphatic radicals A are: 1,3- and 1,4-cyclohexylene, 4-methyl-1,3-cyclohexylene, 2-methyl-1,3-cyclohexylene, 5,5-dimethyl-1,3-cyclohexylene, 2-methyl-1,4-cyclohexylene, 4,6-dimethyl-1,3-cyclohexylene and 4-methyl-1,2-cyclohexylene.

A as a bivalent aryl radical may be a phenylene, biphenylene or naphthylene radical which is unsubstituted or substituted by $C_1$-$C_4$alkyl, $C_1$-$C_4$alkoxy, sulfo, halogen or carboxy.

Exemplary of arylene radicals A are: 1,3- and 1,4-phenylene, 2-sulfo-1,4-phenylene, 4-sulfo-1,3-phenylene, 2-methyl-1,4-phenylene, 2-methoxy-1,4-phenylene, 4,8-disulfo-2,6-naphthylene, 8-sulfo-2,6-naphthylene, 1,4-naphthylene and 1,1'-biphenyl-4,4'-diyl.

An arylene radical A is preferably a 1,3- or 1,4-phenylene radical which is unsubstituted or substituted by sulfo, methyl, methoxy or carboxy, or an unsubstituted or sulfo-substituted naphthylene radical.

Most preferably, an arylene radical A is unsubstituted or sulfo-substituted 1,3- or 1,4-phenylene.

An aralkylene radical A may be a $C_1$-$C_6$alkylene-phenylene, phenylene-$C_1$-$C_6$alkylene-phenylene, $C_1$-$C_3$alkylene-phenylene-$C_1$-$C_3$alkylene or methylene-naphthylene-methylene radical, in which aralkylene radicals the alkylene moiety may be substituted as previously indicated and/or interrupted by one of the aforementioned hetero groups, and the phenylene and naphthylene moiety may additionally carry 1 or 2 substituents selected from the group consisting of sulfo, carboxy, sulfamoyl, carbamoyl, methyl, ethyl, methoxy, ethoxy, nitro, chloro, amino, N-methylamino and N-ethylamino, N,N-dimethylamino and N,N-diethylamino and phenylamino.

Exemplary of suitable aralkylene radicals A are:

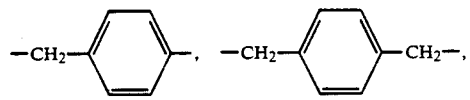

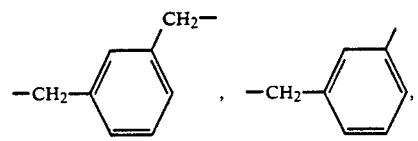

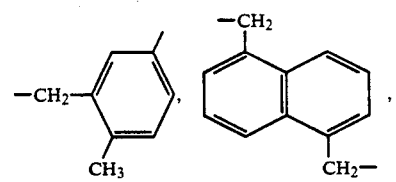

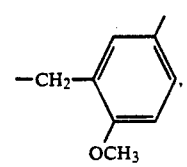

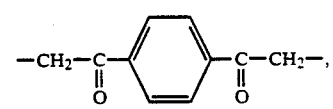

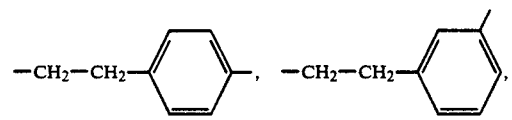

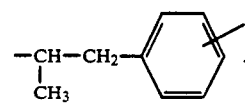

An aralkylene radical A is preferably $C_1$-$C_3$alkylene-phenylene or $C_1$-$C_2$alkylenephenylene-$C_1$-$C_2$alkylene which are unsubstituted or substituted in the phenyl moiety by methyl, methoxy, chloro or sulfo.

A is preferably a $C_2$-$C_4$alkylene radical which is unsubstituted or substituted by hydroxy, sulfo, sulfato, methoxy, carboxy, or sulfophenyl, —$CH_2$—$CH_2$—Z'—$CH_2$—$CH_2$—, wherein Z' is —O—, —S—, —$SO_2$—, —NH— or —N($CH_3$)—, a cyclohexylene radical which is unsubstituted or substituted by 1 to 3 methyl groups, an unsubstituted or sulfo-substituted 1,3- or 1,4-phenylene radical, or a $C_1$-$C_3$alkylene-phenylene or $C_1$-$C_2$alkylene-phenylene-$C_1$-$C_2$alkylene radical, wherein the phenylene moiety is unsubstituted or substituted by methyl, methoxy, chloro or sulfo.

$R_5$ as unsubstituted or substituted alkyl, cycloalkyl, aryl or aralkyl has the meanings and preferred meanings given previously for $R_1$.

$R_5$ is preferably hydrogen, $C_1$-$C_4$alkyl, cyclohexyl, unsubstituted phenyl or benzyl or phenyl or benzyl which are substituted by sulfo, chloro, methyl and/or methoxy.

Particularly preferred meanings of $R_5$ are hydrogen and $C_1$-$C_4$alkyl, more particularly hydrogen, methyl and ethyl and, most preferably, hydrogen.

X is preferably a group —N($R_5$)—, wherein $R_5$ has the meanings and preferred meanings given hereinbefore.

Where the radical

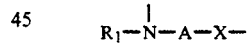

is an unsubstituted or substituted heterocyclic radical, said radical may be piperazin-1,4-diyl.

Y is preferably sulfo, $C_1$-$C_4$-alkyl, $C_1$-$C_4$alkoxy or chloro and, most preferably, methoxy, methyl, chloro or sulfo.

The variable n is preferably 0.

Aryl or aralkyl radicals Z have independently of each other the meanings and preferred meanings previously given for $R_1$.

An unsubstituted or substituted alkyl radical Z may be an unsubstituted or substituted $C_1$-$C_6$alkyl radical, typically a $C_1$-$C_6$alkyl radical which is unsubstituted or substituted by hydroxy, $C_1$-$C_4$alkoxy or carboxy, and which, with the exception of methyl, may be interrupted by —O—, —S— or —N($R_8$)—, wherein $R_8$ is as previously defined.

Preferably an alkyl radical Z is unsubstituted $C_1$-$C_4$alkyl and, more particularly, methyl or ethyl.

Z is preferably methyl or ethyl and, most preferably, hydroxy.

p is preferably 1.

Where $R_2$ and/or $R_3$ are defined as unsubstituted or substituted phenyl, benzyl, benzoylamino or phenoxy, the phenyl ring may be unsubstituted or substituted by $C_1$-$C_4$alkyl, $C_1$-$C_4$alkoxy, acetylamino, halogen, nitro and/or sulfo. Preferably the phenyl ring carries no further substituents or is substituted by chloro, methyl, methoxy, acetylamino and/or sulfo.

The radicals $R_2$ and $R_3$ may be different or, preferably, identical.

$R_2$ and $R_3$ are preferably, however, fluoro, chloro, bromo, methyl, methoxy, acetylamino, phenoxy or cyano and, most preferably, bromo or chloro.

A preferred embodiment of the invention relates to mixture of oligomers of compounds of formula (1), wherein $R_2$ and $R_3$ are each chloro.

The bivalent organic linking group B may be a radical of formula $$-Q-E-Q- \quad (3),$$

wherein E for example is a direct bond, an unsubstituted or substituted alkylene, alkenylene, cycloalkylene, alkylene-cyclohexylene, arylene, aralkylene, heterocyclylene, biphenyl or stilbene radical, Q is a group $$-\overset{O}{\underset{\|}{C}}-, \quad -\overset{O}{\underset{\|}{C}}-N(R_{10})-, \quad -\overset{S}{\underset{\|}{C}}-, \quad -\overset{S}{\underset{\|}{C}}-N(R_{10})-,$$

$$-\overset{O}{\underset{\|}{C}}-O-, \quad -\overset{S}{\underset{\|}{C}}-O-, \quad -\overset{S}{\underset{\|}{C}}-S- \quad \text{or} \quad -\overset{O}{\underset{\underset{O}{\|}}{S}}-$$

and $R_{10}$ is unsubstituted or substituted alkyl, aryl, cycloalkyl or aralkyl, or preferably hydrogen.

Where E is defined as unsubstituted or substituted cycloalkylene, arylene or aralkylene, the meanings and preferred meanings previously given for A apply independently of one another. The alkylene-cyclohexylene, biphenyl or stilbene radicals can be substituted as indicated for A defined as cyclohexylene or arylene.

E defined as alkylene may have one of the meanings previously given for A defined as unsubstituted or substituted alkylene or may be methylene. E defined as alkylene is preferably $C_1$-$C_4$alkylene which is unsubstituted or substituted by hydroxy, sulfo, sulfato, methoxy, carboxy, phenyl or sulfophenyl, and is most preferably methylene, 1,2-ethylene or 1,2- or 1,3-propylene.

A heterocyclyl radical E may be the piperazine-1,4-diyl, furan-2,5-diyl or thiophene-2,5-diyl radical.

$R_{10}$ as unsubstituted or substituted alkyl, cycloalkyl, aryl or aralkyl has the meanings and preferred meanings previously given for $R_1$.

Preferred organic linking groups B are the radicals of formula (3), wherein Q is a group $$-\overset{O}{\underset{\|}{C}}-, \quad -\overset{O}{\underset{\|}{C}}-NH-, \quad -\overset{O}{\underset{\underset{O}{\|}}{S}}- \quad \text{or} \quad -\overset{S}{\underset{\|}{C}}-NH-.$$

E is a direct bond, $C_1$-$C_6$alkylene or $C_2$-$C_6$alkenylene, each unsubstituted or substituted by hydroxy, sulfo, sulfato, methoxy, carboxy, phenyl or sulfophenyl, or is cyclohexylene or $C_1$-$C_2$alkylene-cyclohexylene, each unsubstituted or substituted by 1 to 3 methyl groups, or is piperazine-1,4-diyl, thiophene-2,5-diyl, biphenyl-4,4'-diyl, stilbene-4,4'-diyl, unsubstituted phenylene or naphthylene, or phenylene or naphthylene which are each substituted by $C_1$-$C_4$alkyl, $C_1$-$C_4$alkoxy, sulfo, halogen or carboxy, or $C_1$-$C_3$alkylene-phenylene or $C_1$-$C_2$alkylene-phenylene-$C_1$-$C_2$alkylene, each unsubstituted or substituted in the phenyl moiety by methyl, methoxy, chloro or sulfo.

Especially preferred bivalent linking groups B have the formula $$-O_2S-\underset{R_{11}}{\underset{|}{\bigcirc}}-SO_2-,$$

$$-\overset{O}{\underset{\|}{C}}-NH-\underset{R_{11}}{\underset{|}{\bigcirc}}-NH-\overset{O}{\underset{\|}{C}}-,$$

$$-\overset{O}{\underset{\|}{C}}-\underset{S}{\bigcirc}-\overset{O}{\underset{\|}{C}}-,$$

$$-\overset{S}{\underset{\|}{C}}-NH-\underset{R_{11}}{\underset{|}{\bigcirc}}-NH-\overset{S}{\underset{\|}{C}}-,$$

$$-\overset{O}{\underset{\|}{C}}-NH-\underset{(R_{11})_{0-3}}{\bigcirc}-(CH_2)_{\overline{0-1}}-NH-\overset{O}{\underset{\|}{C}}-,$$

$$-\overset{O}{\underset{\|}{C}}-(CH_2)_{\overline{0-2}}-\underset{R_{11}}{\underset{|}{\bigcirc}}-(CH_2)_{\overline{0-2}}-\overset{O}{\underset{\|}{C}}-,$$

$$-O_2S-\underset{}{\bigcirc\!\!\!\bigcirc}\overset{R_{11}}{\underset{|}{}}-SO_2-,$$

$$-\overset{O}{\underset{\|}{C}}-\bigcirc-\bigcirc-\overset{O}{\underset{\|}{C}}-,$$

$$-\overset{O}{\underset{\|}{C}}-\bigcirc-CH=CH-\bigcirc-\overset{O}{\underset{\|}{C}}-,$$

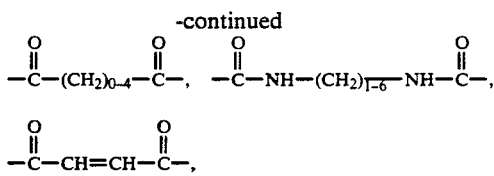

wherein $R_{11}$ is sulfo, methyl, methoxy, chloro, carboxy or, preferably, hydrogen.

A particularly preferred embodiment of the invention relates to mixture of oligomers of compounds of formula (1), wherein B is a radical of formula

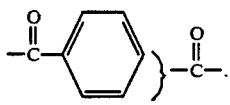

A further group of suitable linking groups B comprises those groups which contain or consist of at least one nitrogen-containing aromatic-heterocyclic radical. Exemplary of such aromatic-heterocyclic linking groups B are a radical of formula

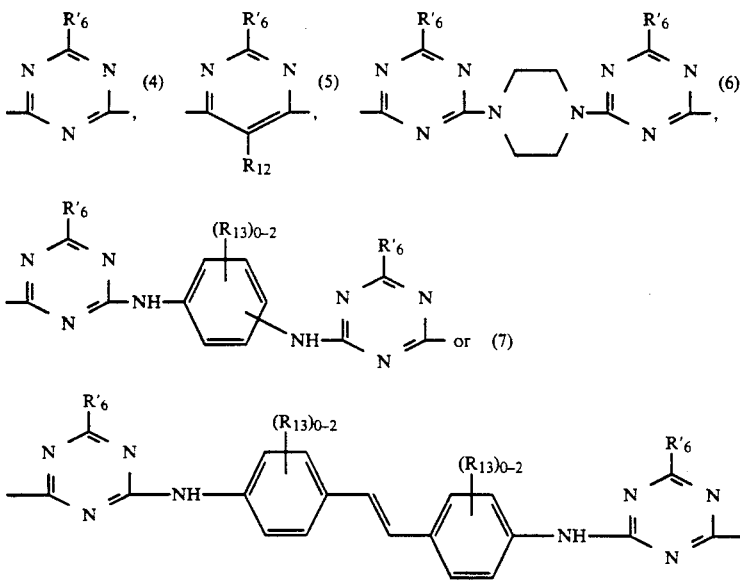

wherein $R_{12}$ is nitro, cyano, $C_1$-$C_4$alkylsulfonyl, carboxy, chloro, fluoro, $C_1$-$C_4$alkoxysulfonyl, $C_1$-$C_4$alkylsulfinyl, $C_1$-$C_4$alkoxycarbonyl or $C_1$-$C_4$alkanoyl and, preferably, cyano, chloro, fluoro, methylsulfonyl, ethylsulfonyl or formyl, $R_{13}$ is sulfo, $C_1$-$C_4$alkyl, $C_1$-$C_4$alkoxy or halogen, preferably sulfo, methyl or methoxy and, most preferably, sulfo, and $R'_6$ is chloro or is as defined for $R_6$ in formula (2). In formulae (4), (5), (6), (7) and (8), $R'_6$ is preferably chloro, hydroxy, $C_1$-$C_4$alkoxy, $C_1$-$C_2$alkylthio, amino, N-mono- or N,N-di-$C_1$-$C_4$alkylamino which are unsubstituted or substituted in the alkyl moiety by hydroxy, sulfo or sulfato, or is cyclohexylamino, phenylamino or N-$C_1$-$C_4$alkyl-N-phenylamino which are unsubstituted or substituted in the phenyl moiety by methyl, methoxy, carboxy, sulfo or chloro, or is morpholino.

Illustrative examples of especially preferred radicals $R'_6$ are hydroxy, chloro, methylthio or ethylthio, methoxy, ethoxy, n- or isopropoxy, amino, methylamino, ethylamino, $\beta$-hydroxyethylamino, N,N-di-$\beta$-hydroxyethylamino, $\beta$-sulfoethylamino, carboxymethylamino, cyclohexylamino, o-, m- or p-methylphenylamino, o-, m- or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino and morpholino.

A further preferred group of useful linking groups B comprises those of formulae

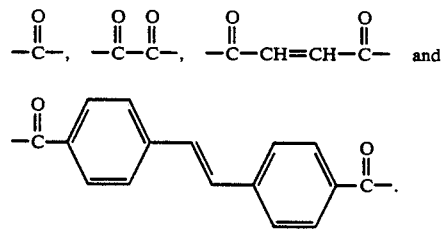

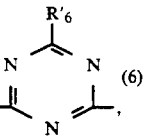

Preferred linking groups B have the formula

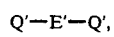

$$Q'-E'-Q', \qquad (3')$$

$$(4')$$

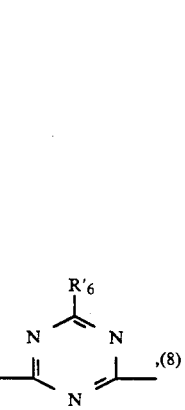

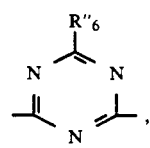

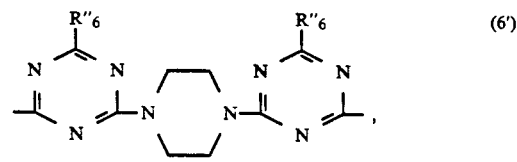

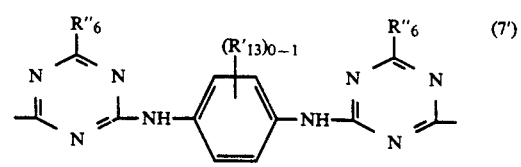

-continued or

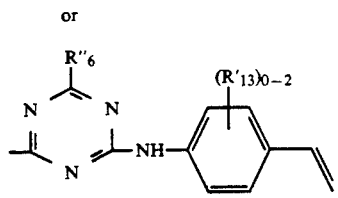
(8')

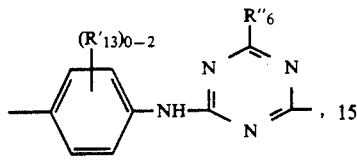

wherein Q' is a group

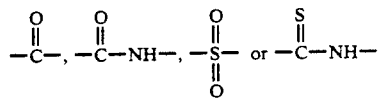

E' is a direct bond, $C_1$–$C_6$alkylene or $C_2$–$C_6$alkenylene which are unsubstituted or substituted by hydroxy, sulfo, sulfato, methoxy, carboxy, phenyl or sulfophenyl, cyclohexylene or $C_1$–$C_2$alkylene-cyclohexylene which are unsubstituted or substituted by 1 to 3 methyl groups, or is piperazine-1,4-diyl, thiophene-2,5-diyl, biphenyl-4,4'-diyl, stilbene-4,4'-diyl, unsubstituted phenylene or naphthylene, or phenylene or naphthylene which are substituted by $C_1$–$C_4$alkyl, $C_1$–$C_4$alkoxy, sulfo, halogen or carboxy, or is $C_1$–$C_3$alkylene-phenylene or $C_1$–$C_2$alkylene-phenylene-$C_1$–$C_2$alkylene which are unsubstituted or substituted in the phenyl moiety by methyl, methoxy, chloro or sulfo, $R''_6$ is chloro, hydroxy, $C_1$–$C_4$alkoxy, $C_1$–$C_2$alkylthio, amino, N-mono- or N,N-di-$C_1$–$C_4$alkylamino which are unsubstituted or substituted in the alkyl moiety by hydroxy, sulfo or sulfato, or is cyclohexylamino, phenylamino or N-$C_1$–$C_4$alkyl-N-phenylamino which are unsubstituted or substituted in the phenyl moiety by methyl, methoxy, carboxy, sulfo or chloro, or is morpholino, and $R'_{13}$ is sulfo, methyl or methoxy.

Particularly preferred bivalent linking groups B are the radicals of formula

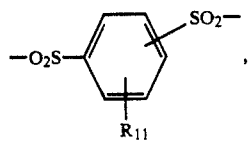

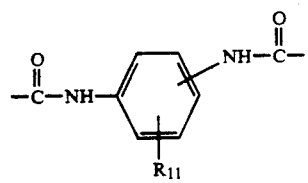

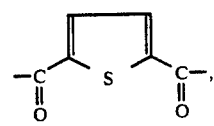

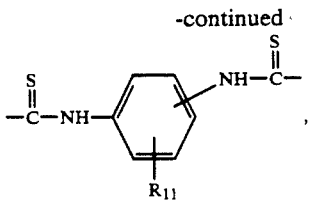

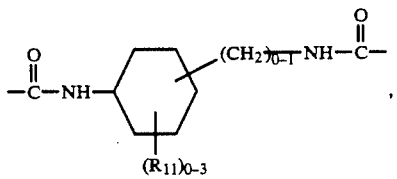

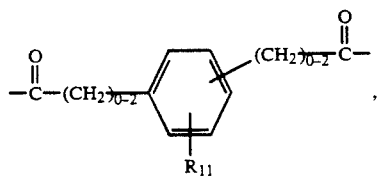

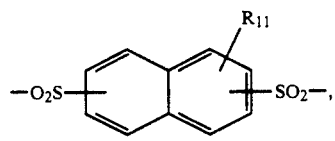

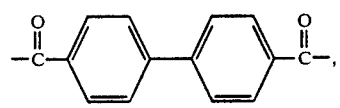

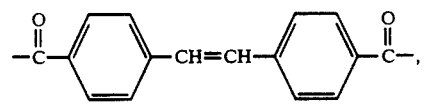

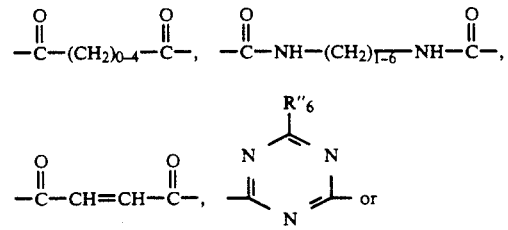

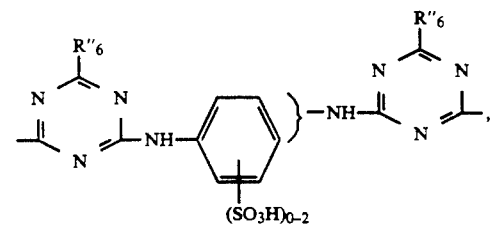

wherein $R_{11}$ is sulfo, methyl, methoxy, chloro, carboxy, or preferably, hydrogen, and $R''_6$ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

m is preferably any integer from 1 to 3.

Because of their good tinctorial properties, important mixtures of oligomers of compounds of formula (1) as indicated above are those wherein $R_1$ is hydrogen, unsubstituted $C_1$–$C_4$-alkyl or $C_1$–$C_4$alkyl which is substituted by hydroxy, sulfo, sulfato, chloro, cyano, or acetoxy and/or, with the exception of methyl, may be interrupted by a group —O—, unsubstituted cyclopentyl or cyclohexyl, or cyclopentyl or cyclohexyl which are substituted by 1 to 3 methyl groups, unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl, or is unsubstituted 1- or 2-naphthyl or 1- or 2-naphthyl which is substituted by sulfo, nitro and/or chloro, or is unsubstituted benzyl or benzyl which is substituted by methyl, methoxy, sulfo and/or chloro, R is hydrogen, $C_1$–$C_4$alkyl, unsubstituted phenyl or benzyl or phenyl or benzyl which are substituted by methyl, methoxy, chloro and/or sulfo, or is a radical of formula

wherein $R_4$ is methyl, ethyl or unsubstituted phenyl or phenyl which is substituted by sulfo, chloro, methyl and/or methoxy, A is a $C_2$–$C_4$alkylene radical which is unsubstituted or substituted by hydroxy, sulfo, sulfato, methoxy, carboxy or sulfophenyl, or is —CH$_2$—CH$_2$—Z′—CH$_2$—CH$_2$—, wherein Z′ is —O—, —S—, —SO$_2$—, —NH— or —N(CH$_3$)—, a cyclohexylene radical which is unsubstituted or substituted by 1 to 3 methyl groups, an unsubstituted or sulfo-substituted 1,3- or 1,4-phenylene radical or is a $C_1$–$C_3$alkylene-phenylene or $C_1$–$C_2$alkylene-phenylene-$C_1$–$C_2$alkylene radical, wherein the phenylene moiety is unsubstituted or substituted by methyl, methoxy, chloro or sulfo, X is a group —N($R_5$)—, wherein $R_5$ is hydrogen, $C_1$–$C_4$alkyl, cyclohexyl, unsubstituted phenyl or benzyl or phenyl or benzyl which are substituted by sulfo, chloro, methyl and/or methoxy, or wherein the group

is the piperazine-1,4-diyl radical, Y is methoxy, methyl, chloro or sulfo, n is 0 or 1, Z is hydroxy, methyl or ethyl, p is 1, $R_2$ and $R_3$ are each hydrogen, fluoro, chloro, bromo, methyl, methoxy, acetylamino, phenoxy or cyano, the linking group B has the formula

Q′—E′—Q′, (3′)

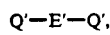

(4′)

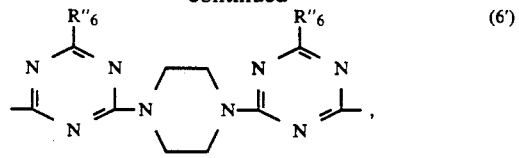 (6′)

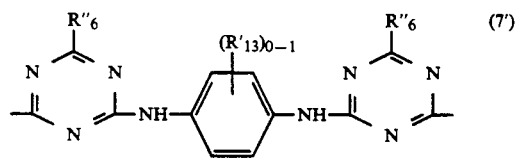 (7′)

or

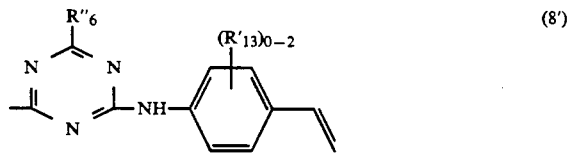 (8′)

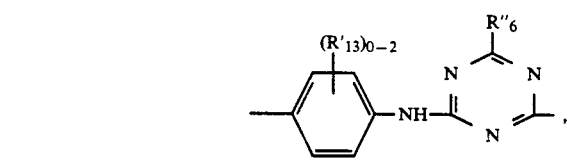

wherein Q′ is a group

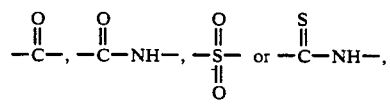

E′ is a direct bond, $C_1$–$C_6$alkenylene which are unsubstituted or substituted by hydroxy, sulfo, sulfato, methoxy, carboxy, phenyl or sulfophenyl, or is cyclohexylene or $C_1$–$C_2$alkylene-cyclohexylene which are unsubstituted or substituted by 1 to 3 methyl groups; piperazine-1,4-diyl, thiophene-2,5-diyl, biphenyl-4,4′-diyl, stilbene-4,4′-diyl; unsubstituted phenylene or naphthylene, or phenylene or naphthylene which are substituted by $C_1$–$C_4$alkyl, $C_1$–$C_4$alkoxy, sulfo, halogen or carboxy; or $C_1$–$C_3$alkylene-phenylene or $C_1$–$C_2$alkylene-phenylene-$C_1$–$C_2$alkylene which are unsubstituted or substituted in the phenyl moiety by methyl, methoxy, chloro or sulfo, R″$_6$ is chloro, hydroxy, $C_1$–$C_4$alkoxy, $C_1$–$C_2$alkylthio, amino, N-mono- or N,N-di-$C_1$–$C_4$alkylamino which are unsubstituted or substituted in the alkyl moiety or moieties by hydroxy, sulfo or sulfato, cyclohexylamino, phenylamino or N-$C_1$–$C_4$alkyl-N-phenylamino which are unsubstituted or substituted in the phenyl moiety by methyl, methoxy, carboxy, sulfo or chloro, or morpholino, and R′$_{13}$ is sulfo, methyl or methoxy, and m is any integer from 1 to 3.

Of particular importance on account of their good tinctorial properties are mixtures of oligomers of the compounds of formula

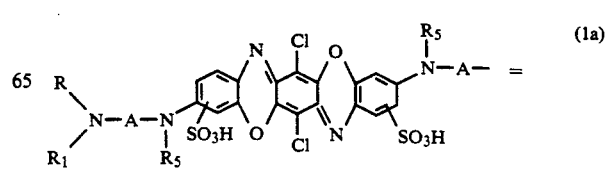 (1a)

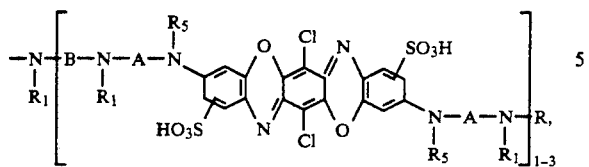

wherein R₁ is hydrogen, C₁-C₄alkyl, cyclohexyl, unsubstituted phenyl or benzyl, or phenyl or benzyl which are substituted by sulfo, chloro, methyl and/or methoxy, R is hydrogen, methyl, ethyl, benzyl, acetylamino or benzoylamino, A is a C₂-C₄alkylene radical which is unsubstituted or substituted by hydroxy, sulfo, sulfato, methoxy, carboxy or sulfophenyl, R₅ is hydrogen, methyl or ethyl, and B is a radical of formula

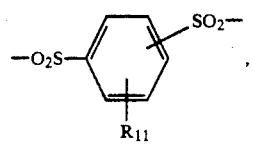

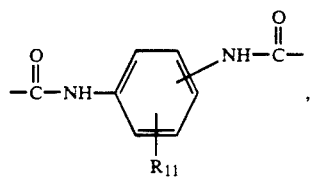

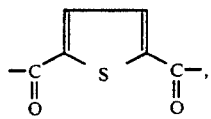

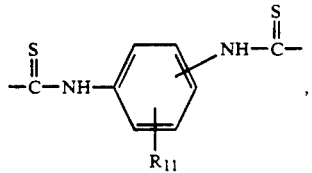

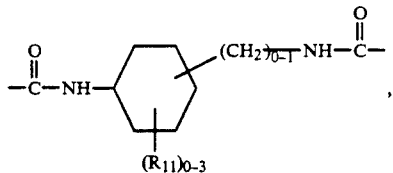

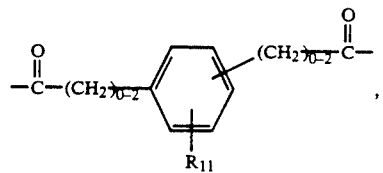

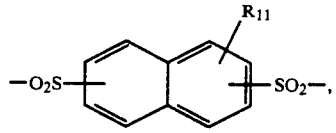

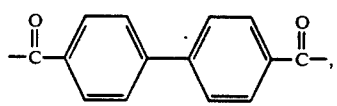

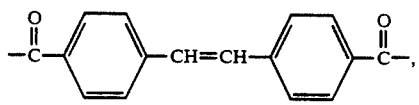

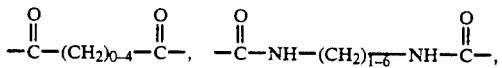

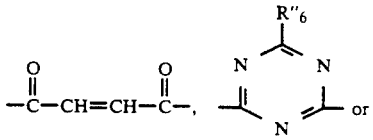

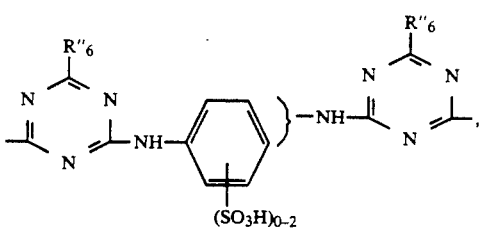

wherein R₁₁ is sulfo, methyl, methoxy, chloro, carboxy or, preferably, hydrogen, and R″₆ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, carboxymethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

A particularly preferred embodiment of the invention relates to mixture of oligomers of compounds of formula

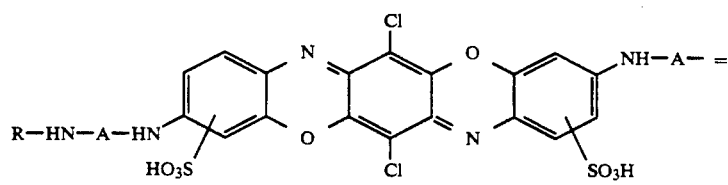

(Ib)

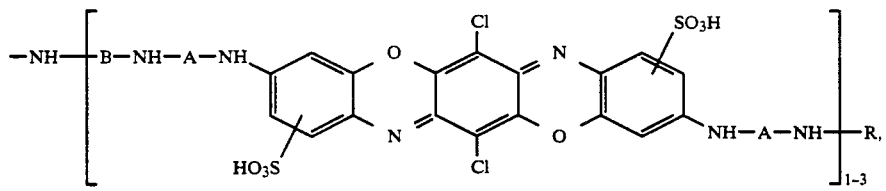

wherein R is methyl, ethyl, benzyl, acetylamino, benzoylamino or, preferably, hydrogen, A is a 1,2-ethylene or 1,2- or 1,3-propylene radical which is unsubstituted or substituted by hydroxy or sulfato, and B is a radical of formula

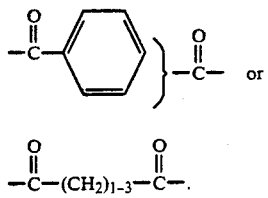

The mixture of oligomers of the compounds of formula (1) may be obtained by condensing a) a compound of formula

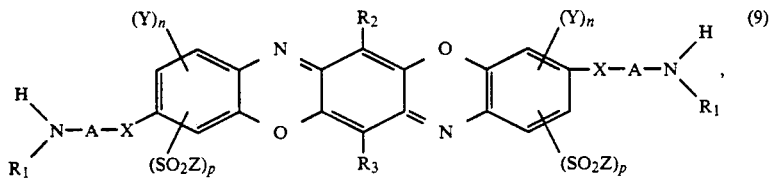

with a compound of formula

    (10), and, in a further optional step, b) reacting the product obtained in a) with a compound of formula

    (11), wherein A, B, $R_1$, $R_2$, $R_3$, X, Y, Z, p and n are each as defined hereinbefore, R* has the meaning previously given for R, with the exception of hydrogen, and T is halogen, preferably chloro.

Preferred mixture of oligomers together contain the three compounds of formula (1), wherein m is 1, 2 and 3.

The condensation reactions a) and b) are conveniently carried out in an aqueous or aqueous-organic medium in the temperature range from 0° to 100° C., preferably from 0° to 50° C. The reactions are conveniently carried out in the neutral to alkaline pH range, i.e. typically at pH 7-13, preferably 8-12. The pH can be adjusted by addition of bases, such as hydroxides or carbonates of alkali metals, ammonia or organic amines, and kept constant during the condensation reactions.

Depending on the weight ratio in which the compounds of formulae (9) and (10) are used, a mixture of oligomers comprising different compounds of formula (1) is obtained in which the value of m differs. The mixture of oligomers comprises typically the six compounds of formula (1) in which m = 1, 2, 3, 4, 5 and 6, the three compounds of formula (1) in which m = 1, 2 or 3 predominating.

In condensation step a), the compounds of formula (1) in which R = hydrogen are obtained. The conversion of the hydrogen atom into any radical R is effected by reaction with a compound of formula (11) in a manner which is known per se.

The compounds of formulae (9), (10) and (11) are known or can be obtained in a manner known per se.

The invention further relates to the use of the mixture of oligomers comprising different compounds of formula (1), in which the value of m differs, as dyes for dyeing or printing nitrogen-containing and, more particularly, hydroxyl group containing fibre materials.

The novel mixtures of different oligomer compounds of formula (1) are thus suitable for dyeing and printing nitrogen-containing or, more particularly, cellulosic fibre materials, preferably textile fibre materials, made of silk, wool or synthetic polyamides, as well as preferably of cellulosic fibres such as rayon, cotton or hemp. With respect to their tinctorial properties, they may be used as direct dyes (C.I. direct dyes).

It is also possible to dye textile fibre materials made from blends, such as wool/cotton, polyamide/cotton, acrylic/cotton or, preferably, polyester/cotton blends, by single bath processes and in the presence of dyes for the respective different type of fibre.

The textile fibre materials may be in any form of presentation, such as fibres, yarn, woven or knitted fabrics. Besides the textile substrates, leather and paper can also be dyed with the dye mixtures of this invention.

Level dyeings in blue shades of good allround fastness properties, especially good fastness to rubbing, wet treatments, wet rubbing, perspiration and light, are obtained. Where necessary, the wetfastness properties, especially washfastness, of the direct dyeings and prints can be substantially enhanced by an aftertreatment with fixing agents.

The novel mixtures of different oligomer compounds of formula (1) have good compatibility with other dyes, especially disperse dyes. The novel dye mixtures have a sufficient high temperature stability and can hence be used for dyeing under the dyeing conditions for polyester fibres, i.e. in the temperature range from c. 100° to 150° C., preferably from 100° to 130° C., from an aqueous liquor and in the pH range from 4 to 7.5, preferably from 5 to 7.

It is thereby possible to use customary disperse dyes together with the dye mixtures of this invention in a single step, one bath process for dyeing polyester/cotton blends, in which process level and fast dyeings are obtained with the respective dye on both types of fibre.

By using a disperse dye of the same shade as the novel dye mixture it is also possible to obtain solid shade dyeings.

The dyeing of textile blends, such as blends of polyester and cellulosic fibres, can be greatly simplified by using the dye mixtures of this invention. The conventional practice of dyeing each component of a fibre blend in a separate procedure under different dyeing conditions is therefore no longer necessary.

The novel mixtures of different oligomer compounds of formula (1) are also suitable for the preparation of aqueous inks for ink-jet printing.

The following Example will serve to illustrate the invention. Unless otherwise indicated, parts and percentages are by weight. The relationship between parts by weight and parts by volume is the same as that between the kilogram and the liter.

EXAMPLE 1 a) 96 parts of 4-(2-aminoethylamino)aniline-3-sulfonic acid are suspended in a mixture of 3000 parts of water and 600 parts of isopropanol, and the suspension is adjusted to pH 5.9 with 13 parts of a phosphate buffer mixture and subsequent addition of 14 parts of an aqueous 4N solution of hydrochloric acid. The batch is then heated to a temperature of 50° C. Then 49.52 parts of chloranil are added and the mixture is stirred for 3 hours, while keeping the pH at 6 by addition of a 2N solution of potassium hydrogencarbonate. The mixture is cooled to c. 40° C., and the product is filtered with suction, washed with 2×200 ml of an aqueous solution of sodium chloride and then once with 200 parts of acetone. The filter product is dried at 40° C., giving a compound of formula

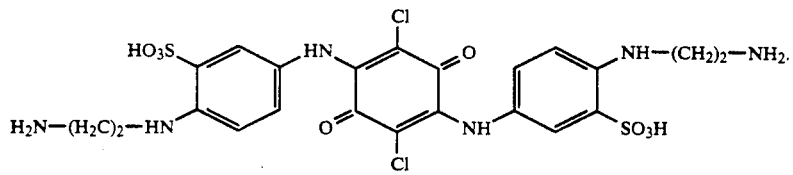
(101)

b) 900 parts of oleum (25%) are charged to the reactor and 166.2 parts of the compound of formula (101) obtained in a) are added in equal portions over 3 hours at a temperature of 0° to 5° C. The mixture is then stirred for 30 minutes at room temperature. Then 118.95 parts of potassium peroxodisulfate are added at 20°-30° C. over 90 minutes and stirring is continued for 75 minutes. The reaction mixture is poured into a mixture of 3000 parts of ice and 600 parts of water, while ensuring that the temperature does not exceed 30° C. The product is filtered with suction and the moist filter product is stirred in 2000 parts of water and the pH is adjusted to 7 with 1400 parts of 30% sodium hydroxide. After stirring overnight the product is filtered with suction, washed with 3×100 parts of water and then with 100 parts of ethanol and dried, to give the compound of formula

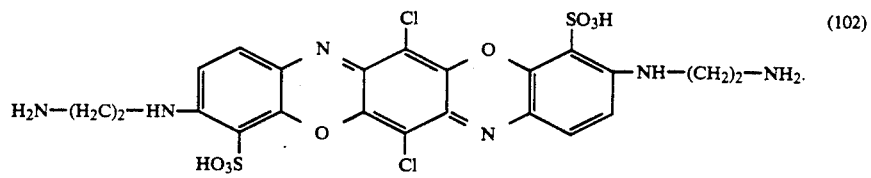
(102)

c) 13.4 parts of the compound of formula (102) obtainable in b) are suspended in 3000 parts of water with the addition of sodium hydroxide solution. A solution of 10.4 parts of terephthaloyl dichloride in c. 150 parts of dioxane is added dropwise at 0° to 5° C. over c. 30 minutes to this suspension, which has a pH of c. 11, while keeping the pH at 11 by adding sodium hydroxide solution. After a reaction time of 1 hour, another solution of 10.4 parts of terephthaloyl dichloride in c. 150 parts of dioxane is added to 0° to 5° C., while keeping the pH at c. 12 by adding sodium hydroxide solution. The batch is allowed to react further once more, the pH is then adjusted to about neutral with hydrochloric acid, and the mixture is stirred for another 30 minutes. The product is then isolated by filtration and dried. It consists of a mixture of oligomer compounds of formula (1), wherein R and $R_1$ are each hydrogen, A is 1,2-ethylene, X is —NH—, n 0, Z is hydroxy, p is 1, $R_2$ and $R_3$ are each chloro and B is a radical of formula

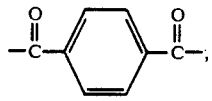

and which dyes cotton in a blue shade of good allround fastness properties.

EXAMPLES 2 TO 11

The procedure of Example 1 is repeated, but replacing in step a) 96 parts of 4-(2-aminoethylamino)aniline-3-sulfonic acid with an equimolar amount of one of the anilino compounds indicated in column 2 of Table 1, to give comparable mixtures of dyes which dye cotton in a brilliant blue shade of good allround fastness properties.

TABLE 1

| Ex. | Anilino compound |
|---|---|
| 2 | $H_2N-\underset{SO_3H}{\bigcirc}-NH-CH_2-\underset{OH}{\overset{|}{CH}}-CH_2-NH_2$ |

TABLE 1-continued

| Ex. | Anilino compound |
|---|---|
| 3 | H₂N—[benzene, SO₃H]—NH—(CH₂)₂—NH₂ |
| 4 | H₂N—[benzene, SO₃H]—NH—(CH₂)₄—NH₂ |
| 5 | H₂N—[benzene, SO₃H]—NH—[cyclohexane]—NH₂ |
| 6 | H₂N—[benzene, SO₃H]—NH—CH₂—CH(CH₃)—NH₂ |
| 7 | H₂N—[benzene, SO₃H]—NH—(CH₂)₂—O—(CH₂)₂—NH₂ |
| 8 | H₂N—[benzene, SO₃H]—NH—(CH₂)₂—NH—(CH₂)₂—OH |
| 9 | H₂N—[benzene, SO₃H]—NH—[benzene, SO₃H]—NH₂ |
| 10 | H₂N—[benzene, SO₃H]—NH—[benzene, HO₃S, SO₃H]—NH₂ |
| 11 | H₂N—[benzene, SO₃H]—NH—[benzene, SO₃H]—(CH₂)₂—NH₂ |

EXAMPLES 12 TO 23

The procedure of Example 1 is repeated, but replacing in step c) 10.4 parts of terephthaloyl dichloride with an equimolar amount of one of the dicarbonyl chloride or disulfonyl chloride compounds indicated in column 2 of Table 2, to give comparable mixtures of dyes dye cotton in a brilliant blue shade of good allround fastness properties.

TABLE 2

| Ex. | Dicarbonyl chloride or disulfonyl chloride compounds |
|---|---|
| 12 | ClOC—[biphenyl]—COCl |
| 13 | ClOC—[benzene]—CH=CH—[benzene]—COCl |
| 14 | ClOC—[thiophene]—COCl |
| 15 | ClOC—COCl (oxalyl chloride) |
| 16 | ClOC—CH₂—[benzene-1,4]—CH₂—COCl |
| 17 | ClOC—CH₂—[benzene-1,3]—CH₂—COCl |
| 18 | ClOC—[benzene]—CH₂—COCl |
| 19 | ClOC—CH=CH—COCl |
| 20 | ClOC—(CH₂)₄—COCl |
| 21 | ClSO₂—[benzene-1,3]—SO₂Cl |
| 22 | [naphthalene-1,5-disulfonyl chloride] |
| 23 | [naphthalene-2,6-disulfonyl chloride] |

EXAMPLE 24

9.74 parts of the compound of formula (102) obtainable as indicated in Example 1 are suspended in 100 parts of water and the suspension is adjusted with 4N lithium hydroxide solution to a pH of 11.5 to 12. The mixture is cooled to a temperature of 15° C., and a solution of 0.93 part of 2,4-toluylene diisocyanate in 10 parts of dioxane are added dropwise with good stirring. When the reaction is complete, the mixture is acidified with hydrochloric acid and the precipitated product is filtered with suction and washed with an aqueous solution of sodium chloride, affording 4 parts of a mixture of oligomer compounds of formula (1), wherein R and $R_1$ are each hydrogen, A is 1,2-ethylene, X is —NH—, n is 0, Z is hydroxy, p is 1, $R_2$ and $R_3$ are each chloro and B is a radical of formula

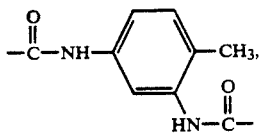

and which dyes cotton in a blue shade of good allround fastness properties.

EXAMPLES 25 TO 30

The procedure of Example 24 is repeated, but replacing 0.93 part of 2,4-toluylene diisocyanate with an equimolar amount of one of the isocyanato or isothiocyano compounds indicated in column 2 of Table 3, to give comparable mixtures of dyes which dye cotton in a brilliant blue shade of good allround fastness properties.

TABLE 3

| Ex. | Isocyanato or isothiocyano compounds |
|-----|---|
| 25 | OCN—⌬—NCO |
| 26 | SCN—⌬—NCS |
| 27 | (3-isomer) NCO, OCN |
| 28 | OCN—(cyclohexyl)—NCO |
| 29 | H₃C, CH₂NCO, CH₃, OCN, CH₃ (trimethylcyclohexyl) |
| 30 | OCN—(CH₂)₆—NCO |

Dyeing instruction I 12.5 parts of a non-mercerised, unbleached cotton fabric are wetted with one part of a nonionic wetting agent at a temperature of 80° C. The cotton is put into a dye solution which contains 2% of the dye mixture obtained in step c) of Example 1 and 2 g/l of sodium sulfate. The liquor ratio is 1:20. The depth is then heated to a temperature of 95° C. over 30 minutes, 8 g/l of sodium sulfate are added and the dyebath is left for 45 minutes at 95° C., cooled to 80° C., and left for 15 minutes at this temperature. The goods are then rinsed with water and dried, to give a cotton fabric which is dyed in a clear blue shade of good allround fastness properties.

Dyeing instruction II 12.5 parts of polyamide 66 fabric are put at 40° C. into a dyebath which has been adjusted to pH 6 by addition of 2 g/l of a phosphate buffer. The liquor ratio is 1:20. After 10 minutes 2% of the dye mixture obtained in step c) of Example 1 are added and the dyebath is heated to the boil over 45 minutes and left for 45 minuts at this temperature. The goods are rinsed with water and dried, to give a polyamide 66 fabric which is dyed in a clear blue shade of good allround fastness properties.

What is claimed is:

1. A mixture of oligomers comprising at least two compounds of formula

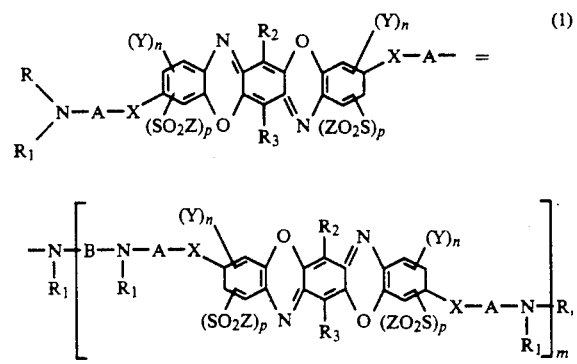

wherein $R_1$ is hydrogen or unsubstituted $C_1$-$C_4$alkyl or $C_1$-$C_4$alkyl which is substituted by hydroxy, sulfo, sulfato, chloro, cyano or acetoxy and, except in the case of $C_1$alkyl or substituted $C_1$alkyl, may be interrupted by a group —O—; cyclopentyl or cyclohexyl which are unsubstituted or substituted by 1 to 3 methyl groups; unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl; unsubstituted 1- or 2-naphthyl or 1- or 2-naphthyl which is substituted by sulfo, nitro or chloro; or unsubstituted benzyl or benzyl which is substituted by methyl, methoxy, sulfo or chloro, R independently has the meaning of $R_1$ or is a pyridine, pyrimidine, quinoxaline or triazine radical each of which is unsubstituted or substituted by hydroxy, $C_1$-$C_4$alkyl, phenyl, $C_1$-$C_4$alkoxy, $C_1$-$C_4$alkylthio, amino, or N-mono- or N,N-di-$C_1$-$C_4$alkylamino which are unsubstituted or substituted in the alkyl moiety or moieties by hydroxy, carboxy, cyano, sulfo, sulfato or $C_1$-$C_4$alkoxy; cyclohexylamino; phenylamino or N-$C_1$-$C_4$alkyl-N-phenylamino which in the phenyl moiety are unsubstituted or substituted by $C_1$-$C_4$alkyl, $C_1$-$C_4$alkoxy, phenoxy, carboxy, sulfo or halogen; morpholino or 3-carboxy- or 3-carbamoylpyridin-1-yl; or R is a radical of formula

wherein R₄ is quinoxaline or pyrimidine or has the meanings given above for R₁, but is not hydrogen, A is a $C_2$-$C_6$alkylene radical which is unsubstituted or substituted by hydroxy, sulfo, sulfato, $C_1$-$C_4$alkoxy, carboxy, cyano, halogen, phenyl, sulfophenyl or $C_2$-$C_5$alkoxycarbonyl, and which is not interrupted or is interrupted by 1 or 2 —O— or —N(R₈)— groups, wherein R₈ is $C_1$-$C_4$alkyl, acetyl or hydrogen, or by —S— or —SO₂—; is a cyclohexylene radical which is unsubstituted or substituted by 1 to 3 methyl groups; or is a phenylene, biphenylene or naphthylene radical which is unsubstituted or substituted by $C_1$-$C_4$alkyl, $C_1$-$C_4$alkoxy, sulfo, halogen or carboxy; or is a $C_1$-$C_6$alkylene-phenylene, phenylene-$C_1$-$C_6$alkylene-phenylene, $C_1$-$C_3$alkylene-phenylene-$C_1$-$C_3$alkylene or methylene-naphthylene-methylene radical, wherein the phenylene and naphthylene moieties contain no further substituents or additionally carry 1 or 2 substituents selected from the group consisting of sulfo, carboxy, sulfamoyl, carbamoyl, methyl, ethyl, methoxy, ethoxy, nitro, chloro, amino, N-methylamino and N-ethylamino, N,N-dimethylamino and N,N-diethylamino and phenylamino, X is —O—, —S— or —N(R₅)—, wherein R₅ has the meanings given above for R₁ or wherein the group

is piperazin-1,4-diyl,

Y is $C_1$-$C_4$alkyl, $C_1$-$C_4$alkoxy, halogen, sulfo, carboxy, carbamoyl, N-mono- or N,N-di-$C_1$-$C_4$alkylcarbamoyl, N-phenyl- or N,N-diphenylcarbamoyl, sulfamoyl, N-mono- or N,N-di-$C_1$-$C_4$alkylsulfonyl or N-phenyl- or N,N-diphenylsulfamoyl, Z is hydroxy or $C_1$-$C_4$alkyl, R₂ and R₃ are each independently of the other hydrogen; halogen; cyano; $C_1$-$C_4$alkyl; $C_1$-$C_4$alkoxy; sulfo; carboxy; carbamoyl; phenylcarbamoyl or $C_2$-$C_5$alkanoylamino; or are phenyl, benzyl, benzoylamino or phenoxy each of which is unsubstituted or substituted in the phenyl ring by $C_1$-$C_4$alkyl, $C_1$-$C_4$alkoxy, acetylamino, halogen, nitro or sulfo, B is a bivalent organic linking group of formula

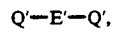

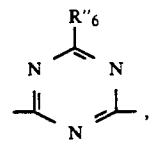

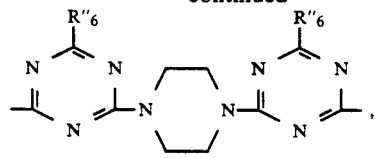

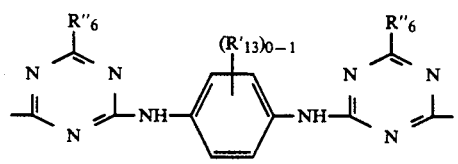

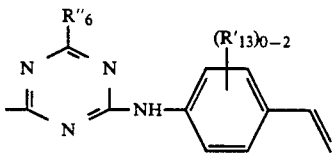

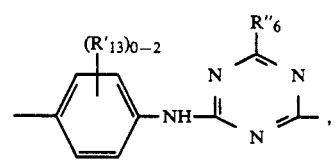

wherein
Q' is a group

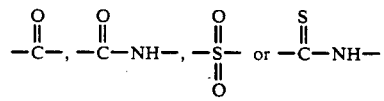

E' is a direct bond; $C_1$-$C_6$alkylene or $C_2$-$C_6$alkenylene which are unsubstituted or substituted by hydroxy, sulfo, sulfato, methoxy, carboxy, phenyl or sulfophenyl; or is cyclohexylene or $C_1$-$C_2$alkylenecyclohexylene which are unsubstituted or substituted by 1 to 3 methyl groups; or is piperazine-1,4-diyl; thiophene-2,5-diyl; biphenyl-4,4'-diyl; stilbene-4,4'-diyl; unsubstituted phenylene or naphthylene, or phenylene or naphthylene which are substituted by $C_1$-$C_4$alkyl, $C_1$-$C_4$alkoxy, sulfo, halogen or carboxy; or is $C_1$-$C_3$alkylene-phenylene or $C_1$-$C_2$alkylene-phenylene-$C_1$-$C_2$alkylene which are unsubstituted or substituted in the phenyl moiety by methyl, methoxy, chloro or sulfo, R″₆ is chloro; hydroxy; $C_1$-$C_4$alkoxy; $C_1$-$C_2$alkylthio; amino; N-mono- or N,N-di-$C_1$-$C_4$alkylamino which are unsubstituted or substituted in the alkyl moiety by hydroxy, sulfo or sulfato; cyclohexylamino; phenylamino or N-$C_1$-$C_4$alkyl-N-phenylamino which are unsubstituted or substituted in the phenyl moiety by methyl, methoxy, carboxy, sulfo or chloro; or is morpholino, R'₁₃ is sulfo, methyl or methoxy, m is an integer from 1 to 6 and n and p are each independently of the other 0 or 1, with the proviso that the different compounds of formula (1) of the mixture of oligomers differ solely in the value of m.

2. A mixture of oligomers according to claim 1, wherein R₁ is hydrogen, $C_1$-$C_4$alkyl, cyclohexyl, unsubstituted phenyl or benzyl, or phenyl or benzyl which are substituted by one or more of sulfo, chloro, methyl and methoxy.

3. A mixture of oligomers of claim 1, wherein $R_1$ is hydrogen.

4. A mixture of oligomers according to claim 1, wherein R is hydrogen, $C_1$-$C_4$alkyl, unsubstituted phenyl or benzyl, or phenyl or benzyl which are substituted by methyl, methoxy, chloro and/or sulfo, or is a radical of formula

wherein $R_4$ is methyl, ethyl or unsubstituted phenyl or phenyl which is substituted by one or more of sulfo, chloro, methyl and methoxy.

5. A mixture of oligomers according to claim 1, wherein R is hydrogen, methyl, ethyl, benzyl, acetylamino, benzoylamino.

6. A mixture of oligomer of claim 5, wherein R is hydrogen.

7. A mixture of oligomers of claim 1, wherein A is a $C_2$-$C_4$alkylene radical which is unsubstituted or substituted by hydroxy, sulfo, sulfato, methoxy, carboxy, or sulfophenyl, —$CH_2$—$CH_2$—$Z'$—$CH_2$—$CH_2$—, wherein $Z'$ is —O—, —S—, —$SO_2$—, —NH— or —N($CH_3$)—, a cyclohexylene radical which is unsubstituted or substituted by 1 to 3 methyl groups, an unsubstituted or sulfo-substituted 1,3- or 1,4-phenylene radical, or a $C_1$-$C_3$alkylene-phenylene or $C_1$-$C_2$alkylene-phenylene-$C_1$-$C_2$alkylene radical, wherein the phenylene moiety is unsubstituted or substituted by methyl, methoxy, chloro or sulfo.

8. A mixture of oligomers of claim 1, wherein A is a $C_2$-$C_4$alkylene radical which is unsubstituted or substituted by hydroxy, sulfo, sulfato, methoxy, carboxy, or sulfophenyl.

9. A mixture of oligomers of claim 1, wherein A is 1,2-ethylene or 1,2- or 1,3-propylene which is unsubstituted or substituted by hydroxy or sulfato.

10. A mixture of oligomers according to claim 1, wherein X is the group —N($R_5$)—, wherein $R_5$ is hydrogen, $C_1$-$C_4$alkyl, cyclohexyl, unsubstituted phenyl or benzyl, or phenyl or benzyl which are substituted by one or more of sulfo, chloro, methyl and methoxy.

11. A mixture of oligomers according to claim 10, wherein $R_5$ is hydrogen or $C_1$-$C_4$alkyl.

12. A mixture of oligomers of claim 11, wherein $R_5$ is hydrogen.

13. A mixture of oligomers of claim 1, wherein n is 0.

14. A mixture of oligomers according to claim 1, wherein p is 1 and Z is hydroxy or $C_1$-$C_4$alkyl.

15. A mixture of oligomers of claim 14, wherein Z is hydroxy.

16. A mixture of oligomers of claim 1, wherein $R_2$ and $R_3$ are each hydrogen, fluoro, chloro, bromo, methyl, methoxy, acetylamino, phenoxy or cyano.

17. A mixture of oligomers of claim 1, wherein $R_2$ and $R_3$ are each chloro.

18. A mixture of oligomers of claim 1, wherein B is a linking group of formula

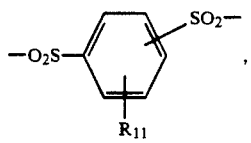

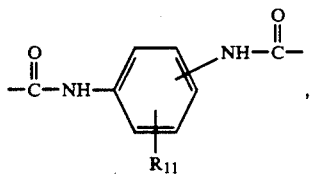

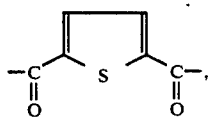

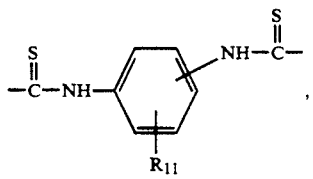

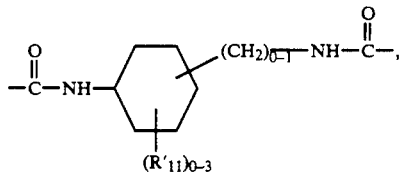

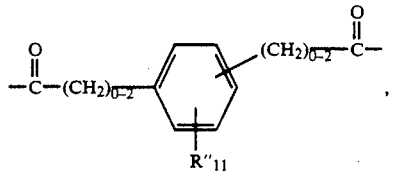

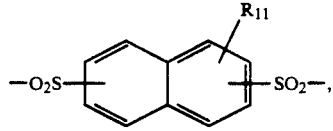

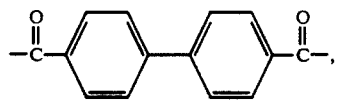

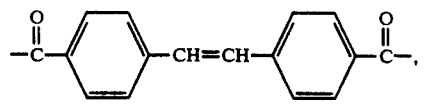

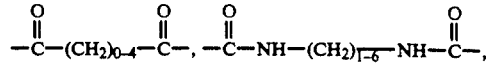

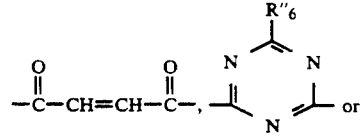

-continued

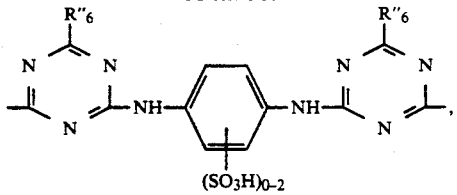

wherein $R_{11}$ is sulfo, methyl, methoxy, chloro, carboxy or hydrogen, $R'_{11}$ is methyl, $R''_{11}$ is methyl, methoxy, chloro or sulfo, and $R''_6$ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, cyclohexylamino, o-, m- or p-methylphenylamino, o-, m-, or p-methylphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

19. A mixture of oligomers of claim 1, wherein B is a radical of formula

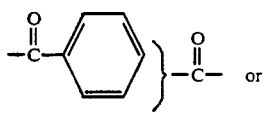 or

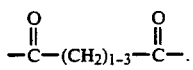

20. A mixture of oligomers of claim 1 of formula (1), wherein $R_1$ is hydrogen, unsubstituted $C_1$–$C_4$alkyl or $C_1$–$C_4$alkyl which is substituted by hydroxy, sulfo, sulfato, chloro, cyano, or acetoxy and, with the exception of $C_1$alkyl, may be interrupted by a group —O—, unsubstituted cyclopentyl or cyclohexyl, or cyclopentyl or cyclohexyl which are substituted by 1 to 3 methyl groups, unsubstituted phenyl or phenyl which is substituted by sulfo, nitro, chloro, methyl, methoxy, N-methylamino or N-ethylamino, N,N-dimethylamino or N,N-diethylamino, acetylamino, propionylamino, benzoylamino, methoxycarbonyl, ethoxycarbonyl, carboxy or methylsulfonyl, or is unsubstituted 1- or 2-naphthyl or 1- or 2-naphthyl which is substituted by sulfo, nitro and/or chloro, or is unsubstituted benzyl or benzyl which is substituted by methyl, methoxy, sulfo and/or chloro, R is hydrogen, $C_1$–$C_4$alkyl, unsubstituted phenyl or benzyl or phenyl or benzyl which are substituted by methyl, methoxy, chloro and/or sulfo, or is a radical of formula $$R_4-\overset{O}{\underset{\|}{C}}-,$$

wherein $R_4$ is methyl, ethyl or unsubstituted phenyl or phenyl which is substituted by sulfo, chloro, methyl and/or methoxy, A is a $C_2$–$C_4$alkylene radical which is unsubstituted or substituted by hydroxy, sulfo, sulfato, methoxy, carboxy or sulfophenyl, or is —CH$_2$—CH$_2$—Z'—CH$_2$—CH$_2$—, wherein Z' is —O—, —S—, —SO$_2$—, —NH— or —N(CH$_3$)—, a cyclohexylene radical which is unsubstituted or substituted by 1 to 3 methyl groups, an unsubstituted or sulfo-substituted 1,3- or 1,4-phenylene radical or is a $C_1$–$C_3$alkylene-phenylene or $C_1$–$C_2$alkylene-phenylene-$C_1$–$C_2$alkylene radical, wherein the phenylene moiety is unsubstituted or substituted by methyl, methoxy, chloro or sulfo, X is a group —N(R$_5$)—, wherein R$_5$ is hydrogen, $C_1$–$C_4$alkyl, cyclohexyl, unsubstituted phenyl or benzyl or phenyl or benzyl which are substituted by sulfo, chloro, methyl or methoxy, or wherein the group $$R_1-\overset{|}{N}-A-X-$$

is the piperazine-1,4-diyl radical, Y is methoxy, methyl, chloro or sulfo, n is 0 or 1, Z is hydroxy, methyl or ethyl, p is 1, $R_2$ and $R_3$ are each hydrogen, fluoro, chloro, bromo, methyl, methoxy, acetylamino, phenoxy or cyano and m is any integer from 2 to 3.

21. A mixture of oligomers according to claim 1 of formula

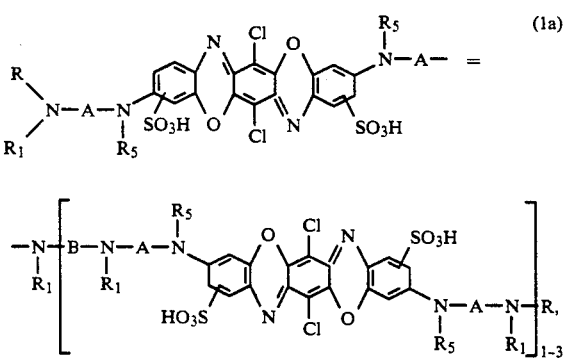

wherein $R_1$ is hydrogen, $C_1$–$C_4$alkyl, cyclohexyl, unsubstituted phenyl or benzyl, or phenyl or benzyl which are substituted by sulfo, chloro, methyl and/or methoxy, R is hydrogen, methyl, ethyl, benzyl, acetylamino or benzoylamino, A is a $C_2$–$C_4$alkylene radical which is unsubstituted or substituted by hydroxy, sulfo, sulfato, methoxy, carboxy or sulfophenyl, $R_5$ is hydrogen, methyl or ethyl, and B is a radical of formula

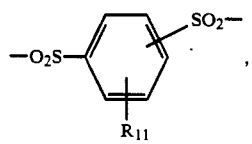

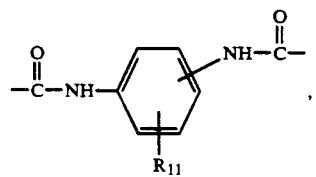

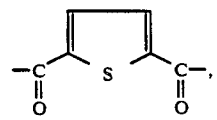

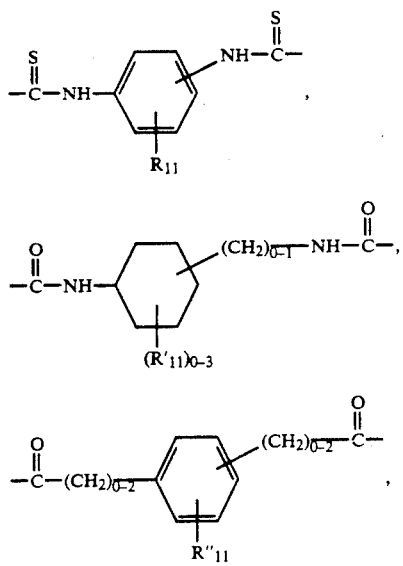

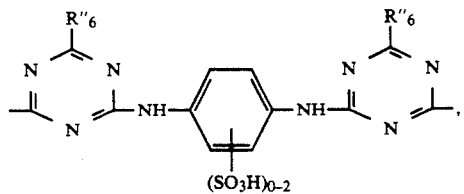

wherein $R_{11}$ is sulfo, methyl, methoxy, chloro, carboxy or hydrogen, $R'_{11}$ is methyl, $R''_{11}$ is methyl, methoxy, chloro or sulfo, and $R'''_6$ is hydroxy, chloro, methylthio or ethylthio, methoxy, ethoxy, n- or isopropoxy, amino, methylamino, ethylamino, β-hydroxyethylamino, N,N-di-β-hydroxyethylamino, β-sulfoethylamino, cyclohexylamino, o-, m- or p-methylphenylamino, o-, m-, or p-methoxyphenylamino, o-, m- or p-chlorophenylamino, o-, m- or p-sulfophenylamino, 2,4- or 2,5-disulfophenylamino, o-carboxyphenylamino, N-ethyl-N-phenylamino, N-methyl-N-phenylamino or morpholino.

22. A mixture of oligomers according to claim 1 of formula

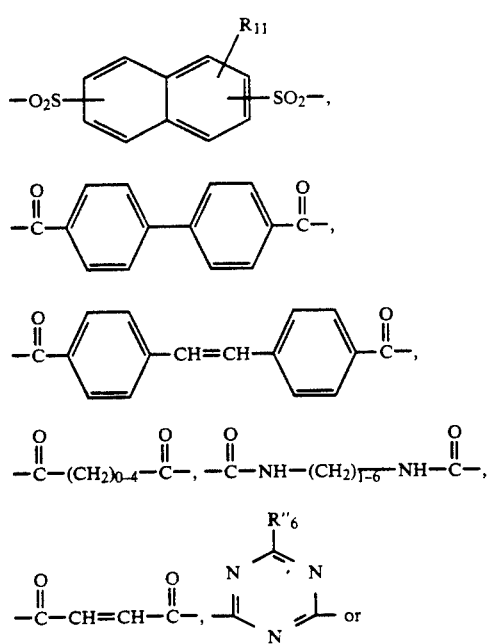

wherein R is methyl, ethyl, benzyl, acetylamino, benzoylamino or hydrogen, A is a 1,2-ethylene or 1,2- or 1,3-propylene radical which is unsubstituted or substituted by hydroxy or sulfato, and B is a radical of formula

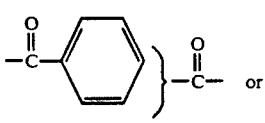

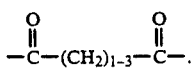

23. A mixture of oligomers of claim 1, which contains a compound of formula (1) wherein m=1, a compound of formula (1) wherein m=2, and a compound of formula (1) wherein m=3.

24. A process for the preparation of a mixture of oligomers of claim 1, which comprises a) condensing a compound of formula

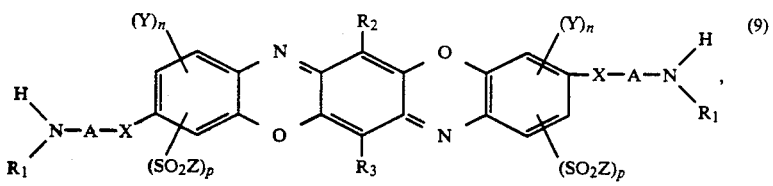

with a compound of formula

T—B—T                     (10), and, in a further optional step, b) reacting the product obtained in a) with a compound of formula

R*—T                      (11), wherein A, B, $R_1$, $R_2$, $R_3$, X, Y, Z, p and n are each as defined hereinbefore, R* has the meaning previously given for R, with the exception of hydrogen, and T is halogen.

25. A method of dyeing or printing nitrogen-containing fibers or cellulose fibers comprising the step of applying to said fibers a mixture of oligomers of claim 1.

26. A method of dyeing or printing a blend of disperse-dyeable synthetic fiber and cellulose fiber, comprising the step of applying a mixture of oligomers of claim 1, in the presence of a disperse dye for the synthetic fiber and under dyeing conditions suitable for dyeing the synthetic fiber with the disperse dye.

27. The method of claim 26, wherein the disperse dyeable synthetic fiber is polyester fiber.

28. A process for dyeing polyester/cotton blends with disperse and direct dyes, which comprises using a mixture of different oligomer compounds of formula (1) as claimed in claim 27 as dye, in a one-step, single bath process and in addition to said disperse dyes, and dyeing from an aqueous liquor in the temperature range from 100° to 150° C., and in the pH range from 4 to 7.5.

29. A process for dyeing polyester/cotton of claim 28, wherein the temperature range is from 120° to 130° C.

* * * * *